United States Patent [19]
Iga et al.

[11] Patent Number: 4,732,760
[45] Date of Patent: Mar. 22, 1988

[54] CURATIVE AND PREVENTIVE AGENT FOR ULCERS OF DIGESTIVE ORGANS

[75] Inventors: Yoshiro Iga, Nishinomiya; Kanemichi Okano, Osaka; Toshiaki Akira, Ibaraki, all of Japan

[73] Assignee: The Green Cross Corporation, Osaka, Japan

[21] Appl. No.: 875,529

[22] Filed: Jun. 20, 1986

Related U.S. Application Data

[63] Continuation of Ser. No. 655,634, Sep. 28, 1984, abandoned.

[30] Foreign Application Priority Data

Nov. 14, 1983 [JP] Japan ................................ 58-213686

[51] Int. Cl.$^4$ ............................................. A61K 35/78
[52] U.S. Cl. ................................ 424/195.1; 514/925; 514/926
[58] Field of Search ............... 424/195.1; 514/925, 514/926

[56] References Cited

PUBLICATIONS

Wren Potter's Cyclopedia, p. 74, 1950.
Claus: Pharmacognosy, 4th Ed., Lea & Febiger, Philadelphia, 1961, p. 219.
Hirschhorn, The Home Herbal Doctor, p. 46, 1982.

*Primary Examiner*—J. R. Brown
*Assistant Examiner*—John W. Rollins
*Attorney, Agent, or Firm*—Cushman, Darby & Cushman

[57] ABSTRACT

A curative and preventive agent for ulcers of digestive organs comprising as the main constituent an active component having anti-ulcer activity derived from a hot-water, an alcohol or a water-alcohol mixed solution extract of cassia buds.

3 Claims, No Drawings

CURATIVE AND PREVENTIVE AGENT FOR ULCERS OF DIGESTIVE ORGANS

This is a continuation of application Ser. No. 655,634, filed Sept. 28, 1984, which was abandoned upon the filing hereof.

BACKGROUND OF THE INVENTION

This invention relates to a curative and preventive agent for ulcers of digestive organs comprising as the main constituent an active component having anti-ulcer activity derived from cassia buds. Cassia buds are immature fruits of *Cinnamomum cassia* Blume belonging to Lauraceae.

The present inventors have heretofore conducted screening of pharmacological effects of a water-soluble component contained in cassia bark, and have consequently found that said component has strong inhibitory activity on gastric acid secretion, improving activity on gastric mucosal blood flow, accelerating activity on gastric mucus secretion and accelerating activity on gastric mucosa restoration, is not at all inferior in inhibitory activity on gastric acid secretion to Cimetidine which is now said to be the most potent as anti-ulcer agent, and has a preventive and curative effect also on stress ulcers and serotonin-induced ulcer.

On the other hand, the active component of this invention was obtained by extracting cassia buds with hot water, an alcohol or a water-alcohol mixed solution and has substantially the same activities as those of the above-mentioned water-soluble component of cassia bark, but was found to give an action spectrum a little different from that of the water-soluble component of cassia bark with respect to anti-ulcer activity on various ulcer model pathologic states obtained by using experimental animals. That is to say, as compared with the water-soluble component of cassia bark, the hot-water extract of cassia buds had a very low inhibitory activity on gastric ulcer induced by loading of cold exposure and restraint stress, had substantially equal inhibitory effect on cysteamine duodenal ulcer, and showed an inhibition percentage of serotonin-induced ulcer due to ischemic lesions of gastric mucosa of 54.3% on the basis of the degree of inhibition in the case of a control group when intraperitoneally administered at the dose of 20 mg/kg. This value indicates that the inhibitory activity of the hot-water extract of cassia buds is as high as 3 times that of the component of cassia bark.

Further, as to toxicity, the hot-water extract of cassia buds is low in toxicity: it showed a 50% lethal dose of 5,000 mg/kg or more when intraperitoneally administered to mice, and hence was concluded to be very high in safety.

From the results described above, it is suggested that the active component having anti-ulcer activity derived from cassia buds improves and increases gastric and duodenal mucosal blood flow to potentiate the preventing abilities and healing powers of digestive organs against ulcer and hence has excellent effects for preventing and healing gastric and duodenal ulcers, whereby this invention has been accomplished.

The object of this invention is to provide a novel curative and preventive agent for mucosal lesions and ulcers in the alimentary tract.

DETAILED DESCRIPTION OF THE INVENTION

According to this invention, there is provided a curative and preventive agent for mucosal lesions and ulcers of digestive organs comprising as the main constituent an active component having anti-ulcer activity obtained by extracting cassia buds with hot water, an alcohol or a water-alcohol mixed solution (hereinafter referred to as "A component").

Cassia buds used as the raw material are dark-brown immature fruits having a diameter of 3 to 5 mm, taste slightly sweet and bitter when crushed with the teeth, and have a cinnamic odor weaker than that of cassia bark. In Kaneyoshi Akamatsu "Japanese and Chinese Medicines" Ishiyaku Publication Co., Ltd., it is described that cassia buds have effects such as nomalization of the functions of the liver in a diseased condition; medical treatment of the stomach lowered in the ability of digestion by stress of cold exposure or by too much fatigue according to the method "Warming" (a method for relieving symptoms of a failure of gastrointestinal functions caused by a cold by using agents for warming the stomach and intestines); assistance to nomalization of renal functions and relief of disorders of digestive funcitons; relief of symtoms of vomitting; relief in pain; and increase of appetite, and that cassia buds are efficatious, for example, against stomachache about the pit of the stomach caused by intemperate eating or drinking or by mental stimulus and against pain accompanied by psychroesthesia due to lowering of the ability of digestion in the stomach caused by stress of cold exposure or by too much fatigue.

One concrete example of a process for obtaining "A component" is as follows.

To 1 kg of dried cassia buds is added 10 liters of water, and extraction was conducted with heating at 50° C. to 100° C. for 1 to 10 hours. Preferably, the mixture is gently boiled for 1 hour. The residue obtained after the extraction was removed by filtration to obtain an extract. Usually, this procedure is repeated twice, and the two extracts thus obtained are combined. In the case of extraction with an alcohol, leaching-out is conducting by using 10 times as much as alcohol as cassia buds at room temperature or a low temperature for 24 to 48 hours to obtain an alcohol extract. After the water or alcohol in these extracts is allowed to evaporate under reduced pressure, the residue is redissolved in water and a dried extract is obtained by freeze-drying. As the alcohol used in the above-mentioned extraction, methanol or ethanol is preferred. Usually, the dried extract is obtained in an amount of 5 to 10% of the weight of dried cassia buds. This extract is stable on storage in a refrigerator at 2° C. to 10° C. and is soluble in water and physiological saline. Depending on the concentration, a small amount of an insoluble material remains, but there is no adverse effect on the efficacy of the extract even when the insoluble material is removed by filtration. In making the dried extract into a medicine, it is made into tablets or capsules by adding thereto an appropriate excipient. It is also possible to make the dried extract into an injection by dissolving it in a physiological isotonic solution, for example, physiological saline.

Further purified "A component" is obtained by purifying the extract obtained in the manner described above by using an appropriate method, for example, adsorption and recovery treatment using silica gel or ion exchange resins such as Amberlite, butanol-water countercurrent fractionation, or the like. Like said extract, "A component" can be made into an internal medicine in the form of tablets or capsules, and may be made into a liquid injection by dissolving it in physiological saline alone or a solution prepared by adding thereto a small amount of a dissolution adjuvant or into a dry injection which is dissolved at the time of use.

The extract of cassia buds and "A component" of this invention (both obtained in Production Examples hereinafter described) were tested for pharmacological effects according to the following methods.

(1) Serotonin ulcer

Serotonin.creatinine sulfate, at the dose of 30 mg/kg, was subcutaneously administered to the dorsal part of male Wistar strain rats weighing 160 to 180 g fasted for 48 hours prior to the experiment, and after 4 to 24 hours, the rats were subjected to laparotomy for evaluating the drug potency. The ulcer index was expressed in terms of the sum total of the areas of hemorrhagic erosions. Each test sample (the hot-water extract, "A component" or physiological saline as control) was intraperitoneally administered 30 minutes before the administration of serotonin.

(2) Stress ulcer induced by cold exposure and restraint

Male SD strain rats weighing 160 to 180 g fasted for 24 hours were restrained in a cage made of wire net, left as they were in a cold room at $4 \pm 1°$ C. for 5 hours, and then subjected to laparotomy followed by assay. The ulcer index was expressed in terms of the sum total of the major axes of hemorrhagic erosions. Each test sample was intraperitoneally administered 30 minutes before the beginning of the restraint.

(3) Cysteamine-induced duodenal ulcer

Cysteamine hydrochloride was administered to female Wistar strain rates (body wt. 250 to 300 g) fasted for 24 hours under the skin of the back in an amount of 40 mg/kg, 18 hours after which the rats were subjected to laparotomy, and the areas of erosions formed in the duodenal portion were measured. Each test sample was intraperiotoneally (I.P.) administerred 30 minutes before the administration of cysteamine hydrochloride.

The test results of above (1), (2) and (3) are shown in Table 1, Table 2 and Table 3, respectively.

TABLE 1

| Inhibition test of Serotonin ulcer | |
|---|---|
| Test sample | 84% Inhibition dose ($ID_{84}$) |
| Hot-water extract of cassia buds | 41.0 mg/kg I.P. |
| "A component" | 0.03 mg/kg I.P. |
| Hot-water extract of cassia bark | 162.5 mg/kg I.P. |

TABLE 2

| Inhibition test of stress ulcer induced by cold exposure and restraint | |
|---|---|
| Test sample | 84% Inhibition dose ($ID_{84}$) |
| Hot-water extract of cassia buds | Ineffective |
| Hot-water extract of cassia bark | 84.4 mg/kg I.P. |

TABLE 3

| Inhibition test of cysteamine-induced duodenal ulcer | |
|---|---|
| Test sample | 84% Inhibition dose ($ID_{84}$) |
| Hot-water extract of cassia buds | 34.9 mg/kg I.P. |

TABLE 3-continued

| Inhibition test of cysteamine-induced duodenal ulcer | |
|---|---|
| Test sample | 84% Inhibition dose ($ID_{84}$) |
| Hot-water extract of cassia bark | 34.7 mg/kg I.P. |

As shown above, the hot-water extract of cassia buds and "A component" exhibited a very high inhibitory effect on serotonin ulcer. This indicates that these substances and components improve and sufficiently maintain microcirculation of blood in the gastric and duodenal mucosae and bring about the ability of resistance to ulceration, and they are very useful and effective as medicines for remedy and prevention of relapse of gastric and duodenal ulcers.

Although the effective dose of the hot-water extract or "A component" varies depending on symptoms to be cured or prevented, the effective dose of the extract is usually more than 10 mg/kg/day, preferably 40 to 50 mg/kg/day, and that of "A component" is usually more than 0.01 mg/kg/day, preferably 0.05 to 0.1 mg/kg/day.

This invention is further explained in more detail referring to Production Examples and Examples, which are not by way of limitation but by way of illustration.

PRODUCTION EXAMPLE 1

To 50 kg of cassia buds were added 100 liters of water, and extraction was conducted with heating at 100° for 1 hour. This extraction procedure was repeated twice to obtain 200 liters of an extract. This extract was condensed under reduced pressure to a volume of about 20 liters. (The condensed extract was used as the hot-water extract in the experimental example). The condensed extract was centrifuged (7,000 r.p.m., 10 min), after which the supernatant was recovered, and 12,000 $cm^3$ of Amberlite XAD-2 (manufactured by ORUGANO K.K.) was added to adsorb "A component". After rinsing, "A component" was eluted by addition of 80% methanol and then the eluate was separated and concentrated, and 420 g of silica gel (manufactured by Merck & Co., Inc.) was added thereto to adsorb "A component".

The silica gel adsorbing "A component" was placed on a column packed with 6 kg of silica gel and eluted by allowing 45 liters of methanol to flow through the column, and the eluate was evaporated to dryness under reduced pressure. Then, 2 liters of water were added to dissolve the dried eluate, and the resulting solution was extracted 5 times with butanol, after which the combined butanol layer was recovered. The butanol was removed by distillation under reduced pressure, and the residue was dissolved in 1 liter of water. The resulting solution was introduced into an Amberlite XAD-2 column and eluted with an 80% aqueous methanol solution to obtain 10 liters of an eluate.

The eluate was evaporated to dryness under reduced pressure and then dissolved in 20 ml of a 50% aqueous methanol solution. The resulting solution was brought into contact with a Toyopearl HW-40S (manufactured by TOYOSODA K.K.) to adsorb "A component", which was then eluted with 50% aqueous methanol solution and recovered. (This product was used as "A component" in the experimental example).

PRODUCTION EXAMPLE 2

To 1 kg of cassia buds were added 10 liters of ethanol, and the resulting mixture was gently stirred at 60° C. for 3 hours to obtain an ethanol extract. The extract was evaporated under reduced pressure and then redissolved in water, and the resulting solution was freeze-dried to obtain 100 g of a dried extract.

PRODUCTION EXAMPLE 3

Ten liters of a 50% aqueous ethanol solution were added to 1 kg of cassia buds and leaching-out was conducted at room temperature for 24 to 48 hours to obtain a water-alcohol mixed solution extract. The extract was evaporated to dryness under reduced pressure and then redissolved in water, and the resulting solution was freeze-dried to obtain 95 g of a dried extract.

EXAMPLE 1

Oral medicine

| | |
|---|---|
| (1) Hot water extract of cassia buds | 100 mg |
| (2) Fine grains No. 209 for direct tabletting (mfd. by FUJI KAGAKU K.K.) | 46.6 mg |
| metasilisic acid magnesium aluminate | 20% |
| corn starch | 30% |
| lactose | 50% |
| (3) Crystalline cellulose | 24.0 mg |
| (4) Carboxymethyl cellulose.calcium | 4.0 mg |
| (5) Magnesium stearate | 0.4 mg |

All of (1), (3) and (4) were previously passed through a 100-mesh screen. These (1), (3) and (4) and (2) were individually dried to a definite water content and were then mixed in the above-mentioned weight proportion by means of a mixer. Subsequently, (5) was added to the entirely homogeneous mixed powder thus obtained and mixed therewith for a short period of time (30 minutes), and the resulting mixed powder was tabletted (pounder: 6.3 mm, 6.0 mm R) to obtain tablets. If necessary, the tablets may be coated with conventional film coating agents soluble in the stomach (e.g., polyvinyl acetal diethyaminoacetate) or edible coloring agents.

EXAMPLE 2

Oral tablets were prepared in the same manner as in Example 1, except that (1) in Example 1 was replaced by 100 mg of a methanol extract of cassia buds or by "A component" in an amount of 0.1 to 100 mg depending on its efficacy.

EXAMPLE 3

| | |
|---|---|
| (1) 50% Aqueous methanol solution extract of cassia buds | 50 g |
| (2) Lactose | 935 g |
| (3) Magnesium stearate | 15 g |

The above-mentioned components of (1), (2) and (3) were individually weighed out and 1,000 g, in all, of these were homogeneously mixed, after which the resulting mixed powder was packed into capsules made of hard gelatine in an amount of 200 mg each to prepare oral capsules.

EXAMPLE 4

Oral capsules were prepared in the same manner as in Example 3, except that (1) in Example 3 was replaced by 50 g of a methanol extract of cassia buds or by "A component" in an amount of 50 to 10,000 mg depending on its efficacy.

EXAMPLE 5

Injection

A vial or ampoule dried medicine of "A component" was prepared, immediately dissolved in distilled water or physiological saline, and used as an injection.

EXAMPLE 6

Injection

An injection accoridng to the Japanese Pharmacopoeia was prepared by making "A component" alone or together with appropriate stabilizer and isotonicity, into an aqueous solution, and filling the solution into ampoules.

What is claimed is:

1. A method of preventing or inhibiting mucosal lesions and ulcers of the digestive organs which method comprises administering from 10 to 50 mg/kg/day to a person in need of same, of an extract having anti-ulcer activity extracted from cassia buds with hot water, an alcohol or a mixed water-alcohol solution, the alcohol being selected from the group consisting of methanol and ethanol.

2. The method of claim 1 in which the ulcers are gastric ulcers.

3. The method of claim 1 in which the ulcers are duodenal ulcers.

* * * * *